(12) United States Patent
Gershlick

(10) Patent No.: US 10,835,399 B2
(45) Date of Patent: Nov. 17, 2020

(54) BRANCH STENT

(71) Applicant: University Hospitals of Leicester NHS Trust, Leicester (GB)

(72) Inventor: Anthony Gershlick, Leicester (GB)

(73) Assignee: University Hospitals of Leicester NHS Trust, Leicester (GB)

( * ) Notice: Subject to any disclaimer, the term of this patent is extended or adjusted under 35 U.S.C. 154(b) by 0 days.

(21) Appl. No.: 16/072,937

(22) PCT Filed: Jan. 20, 2017

(86) PCT No.: PCT/EP2017/051161
§ 371 (c)(1),
(2) Date: Jul. 26, 2018

(87) PCT Pub. No.: WO2017/129484
PCT Pub. Date: Aug. 3, 2017

(65) Prior Publication Data
US 2019/0029853 A1 Jan. 31, 2019

(30) Foreign Application Priority Data
Jan. 26, 2016 (GB) .................................. 1601471.4

(51) Int. Cl.
*A61F 2/915* (2013.01)
*A61F 2/82* (2013.01)
*A61F 2/856* (2013.01)

(52) U.S. Cl.
CPC .............. *A61F 2/915* (2013.01); *A61F 2/856* (2013.01); *A61F 2002/821* (2013.01); *A61F 2002/825* (2013.01); *A61F 2002/91525* (2013.01); *A61F 2002/91533* (2013.01); *A61F 2002/91541* (2013.01); *A61F 2002/91558* (2013.01); *A61F 2002/91566* (2013.01);
(Continued)

(58) Field of Classification Search
CPC ........ A61F 2002/821; A61F 2250/0065; A61F 2002/91525; A61F 2/915; A61F 2/954; A61F 2002/826; A61F 2250/0006–008; A61F 2250/0036–0039
See application file for complete search history.

(56) References Cited

U.S. PATENT DOCUMENTS

2007/0061003 A1    3/2007   Shmulewitz et al.
2007/0088428 A1    4/2007   Teichman
(Continued)

OTHER PUBLICATIONS

International Search Report and Written Opinion dated Jun. 12, 2017 for International Application No. PCT/EP2017/051161, 20 pages.

*Primary Examiner* — Jerrah Edwards
*Assistant Examiner* — Rebecca S Preston
(74) *Attorney, Agent, or Firm* — McDonnell Boehnen Hulbert & Berghoff LLP

(57) ABSTRACT

This disclosure relates to a stent for use in vascular interventions, the stent comprising a first portion for placing in a first lumen and a second portion for placing in a region of a branch point at which the first lumen branches off a second lumen, the second portion comprising one or more rings linked by second links to the first portion and, if the second portion comprises two or more rings, together. The first and second portions are configured to be different to facilitate controlled longitudinal deformation of the second portion.

18 Claims, 3 Drawing Sheets

(52) U.S. Cl.
CPC ............... *A61F 2002/91575* (2013.01); *A61F 2210/0014* (2013.01); *A61F 2250/001* (2013.01); *A61F 2250/0006* (2013.01); *A61F 2250/0018* (2013.01); *A61F 2250/0029* (2013.01); *A61F 2250/0036* (2013.01); *A61F 2250/0048* (2013.01)

(56) References Cited

U.S. PATENT DOCUMENTS

| | | | |
|---|---|---|---|
| 2008/0167707 A1* | 7/2008 | Marrey | A61F 2/91 623/1.16 |
| 2010/0004728 A1* | 1/2010 | Rao | A61F 2/07 623/1.11 |

* cited by examiner

BRANCH STENT

This application is a national stage application under 35 U.S.C. § 371 of International Patent Application No. PCT/EP2017/051161, filed Jan. 20, 2017, which claims priority to United Kingdom Patent Application No. 1601471.4, filed Jan. 26, 2016.

The present disclosure relates to a stent for use in vascular interventions, such as vascular surgery, in particular although not exclusively for placement in a branch lumen branching off a main lumen.

Vascular interventions using a stent in a branched vessel system, in particular in a side branch vessel branching off a main branch vessel, is known to be more difficult than using a stent in a region where no branching occurs. Vascular interventions may include, but are not limited to, vascular surgery.

For two stent techniques to treat bifurcations the difficulty arises in connection with maintaining an open lumen in both the side and main branches, ensuring that a stent in the side branch does not protrude into the main branch while covering the side branch up to and including the ostium between the side and main branches Excess stent material at the bifurcation can thus result from using a two stent technique with standard stents leading to multiple layers of stent material in the main branch. For example a known approach is to crush any portion of the side branch stent protruding into the main branch with a balloon inflation in the main branch. This leaves the crushed stent material in the main branch and therefore is associated with a degree of obstruction. In another technique known as the "Culotte" there may also be a degree of mal-apposition of the stent material around the opening of the side branch, with a potential to lead to re-stenosis of the lumen at this site. Yet other approaches have been based on complicated linkages between main and side branch stents A novel approach has been described in WO2008/149094, incorporated herein by reference, in which the side branch stent is arranged to conform to the opening of the side branch while maintaining the angle between the side branch and main branch angle, so that side branch stent is flush with the main branch lumen. The novel side branch stent is modified by a balloon inflated in the main branch with the side branch stent in position Aspects of the disclosure relates to a stent for use in vascular interventions, the stent comprising a first portion for placing in a first lumen and a second portion for placing in a region of a branch point at which the first lumen branches off a second lumen, the second portion comprising one or more rings linked by second links to the first portion and, if the second portion comprises two or more rings, together.

The second portion may comprise, one, two or more rings and the rings in the second portion may be defined by a meander pattern extending between opposed bends spaced apart along the stent. The first portion may comprise a plurality of rings linked together by first links, each ring being defined by a meander pattern extending between opposed bends spaced apart along the stent. The meander pattern may comprise repeated S-shaped segments with adjacent segments joined together, for example along a centre line of the meander pattern.

The second portion may be configured to deform by foreshortening longitudinally to conform with an ostium between the first and second lumen while remaining substantially to conform with the first lumen when the stent has been placed and expanded with the second portion in the region of the branch point and a balloon catheter is inflated in the second lumen to conform the second portion to the ostium.

In a first aspect, each second link comprises three straight portions joined by a bend between each pair of straight portions. Advantageously, by having two or more bends and a corresponding number of straight portion, the lateral excursion of the bends for a given longitudinal travel of the ring attached to the link is reduced, thus facilitating the maintenance of conformity with the lumen/vessel surface as the rings are displaced to conform the free end of the second portion to the ostium by balloon inflation in the main branch.

In a second aspect, bends on one side of each ring in the first portion are aligned with bends on an adjacent side of an adjacent ring in the first portion and bends on one side of each ring in the second portion are aligned with bends on a far side of an adjacent ring in the second portion. Advantageously, the relative orientation of the rings in the first portion facilitates an increased stiffness of the first portion while the relative orientation of the rings in the second portion provides a relatively more flexible second portion to facilitate conforming the second portion to the region of the first lumen near the branch point and the ostium.

In a third aspect, respective meander lengths along the meander pattern of the one or more rings in the second portion are greater than respective meander lengths along the meander pattern of rings in the first portion. As a result, the length of material defining the ring(s) in the second portion is longer than in the first portion, which facilitates shaping the stent to expand towards the ostium as it is placed and expanded, facilitating improved conformity with the shape of the side branch in the region of the ostium and/or the region around the ostium in the main branch, in particular by enabling a hyper-extension of the second portion in the region of its free end.

In a fourth aspect, the second links have a second width that is less than that of the first links. By making the material width in the second portion smaller than in the first portion, the second portion can be made more malleable while maintaining structural stability and rigidity of the first portion than would otherwise be possible. This facilitates conforming the second portion to the region of the second lumen near the ostium and the ostium itself, for example by respective balloon inflations.

It will be appreciated that each of the above aspects contributes to facilitating malleability of the second portion to enable a controlled longitudinal shaping of the second portion by applied pressure from the main branch (e.g. using a balloon catheter) in a way that facilitates conformity of the second portion with the second lumen and the ostium. Likewise, the combination of any one or more of these aspects is equally envisaged, each aspect contributing in a different way to achieve controlled malleability of the second portion in a way that facilitates conforming the second portion to the second lumen and ostium.

In a fifth aspect, the second portion comprises third links, each third link linking a second link with another second link or with one of the rings in the first or second portion. Advantageously, this facilitates a reduction in cell size (the area of empty space between adjacent second links and corresponding rings) while maintaining controlled malleability. Reduced cell size may be advantageous in terms of better support for vessel tissue and/or more efficacious delivery of eluted drug (in a drug eluting stent). For example, third links between second links may take three straights/two bends (or at least three/two) shape ("z" shape) or a portion of the third link may be provided as a hollow quadrilateral structure, such as a hollow flat diamond shape. It will be appreciated that the fifth aspect can be combined with any one or more of the first to fourth aspects and that the benefits provided by the fifth aspect equally accrue in such combinations in a synergistic manner, since controlled malleability can be combined with reduced cell size.

Specific embodiments are now described by way of example and with reference the accompanying Figures, in which.

Figures 1A, 1B, 1C:
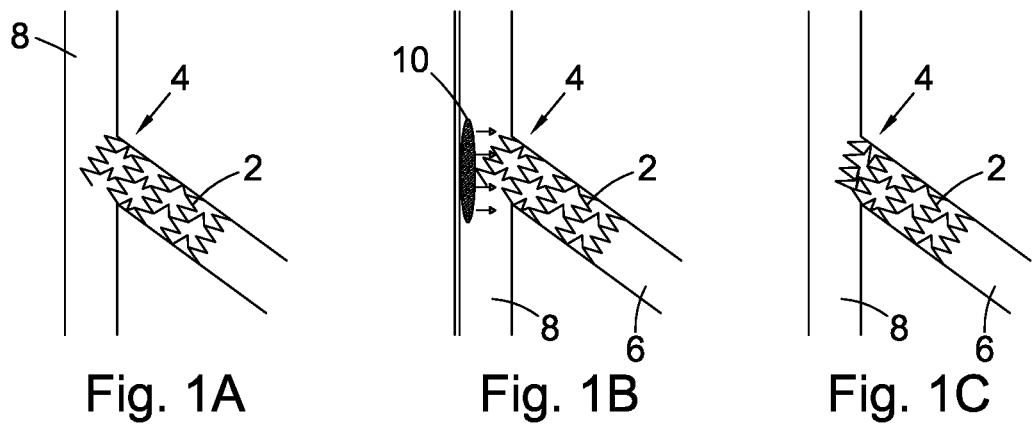
FIGS. 1A, 1B and 1C illustrate a method of placing a stent having a malleable end in a side branch.

With reference to FIG. 1A, a stent 2 having a malleable end 4 has been placed and expanded in a lumen 6 of a branch vessel such that it fully covers the lumen 6 and approximately aligns on one side of the stent with an ostium between the lumen 6 and a lumen 8 of a main vessel from which the branch vessel branches off at a branch point. In particular on the other side of the stent, the stent protrudes into the lumen 8.

With reference to FIG. 1B, subsequent to placement of the stent 2 in the lumen 6, a balloon 10 is introduced in the main branch lumen 8. The balloon is inflated to exert a pressure on the malleable end 4 of the stent 2 in order to longitudinally deform the malleable end 4 to conform to the ostium (leaving the lumen 8 of the main branch vessel substantially open). The stent is configured so as to longitudinally yield in response to the applied pressure while remaining substantially conform with the vessel wall of the branch vessel, as illustrated in FIG. 1C. As a result, the free end of the malleable end 4 is left flush with the ostium of the lumen 6, and is no longer protruding into the lumen 8.

Figure 2A:
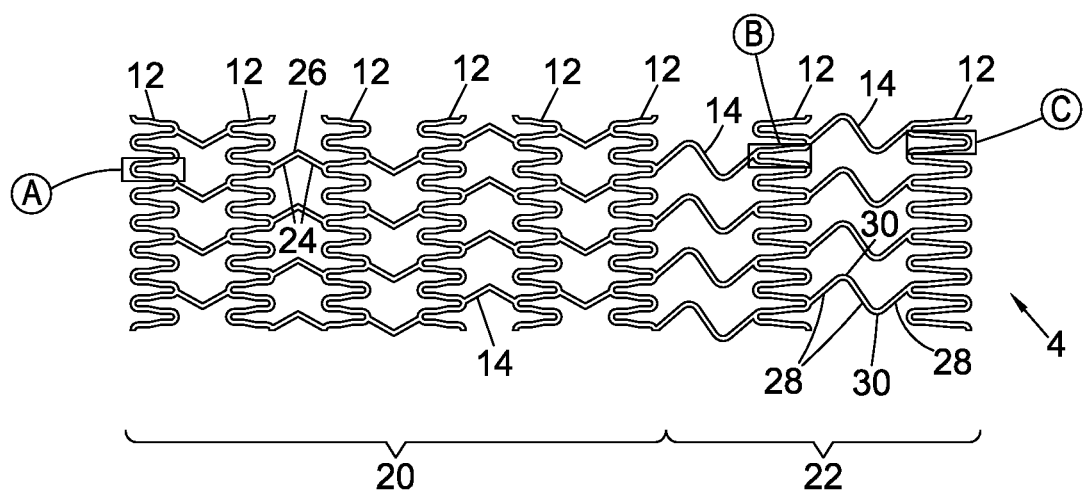
FIGS. 2A to 2C illustrate a stent design with a malleable end.
Figure 2B:
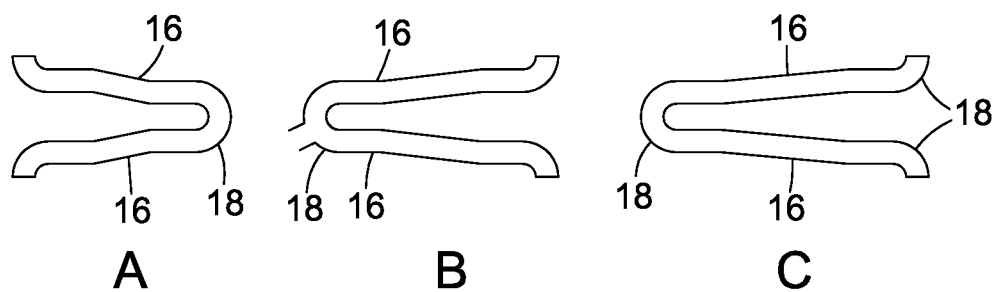
Figure 3:
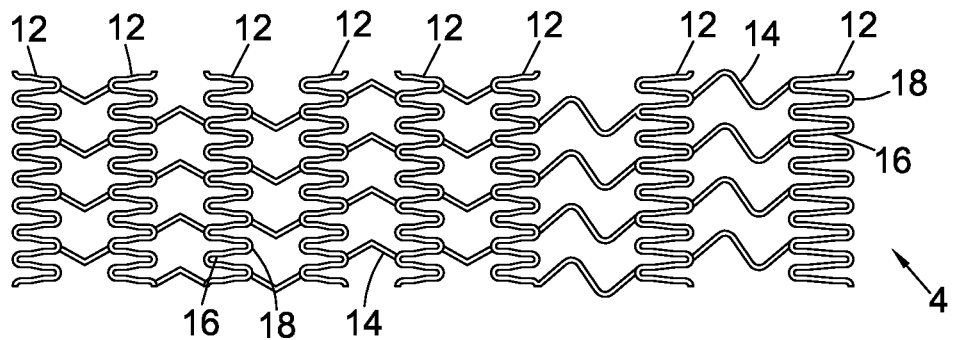
FIG. 3 illustrates a further stent design with a malleable end.

With reference to FIGS. 2A and 2B (showing an enlarged inserts A, B and C), a design for a stent 2 having a malleable end 4 is now described. It will be appreciated that FIG. 2A depicts a portion of a repeating pattern formed in a sheet of material, typically metal, for example a memory alloy or other alloy, in particular highly ductile and corrosion resistant alloys, such as Cobalt Chromium L605, and that the stent 2 is formed by rolling the repeated pattern of material into a tubular configuration, securing the free lateral ends of the pattern together, for example by welding. Reference will be made to FIG. 2A (and FIG. 3) referring to the stent 2 formed from the pattern.

Figure 2C:
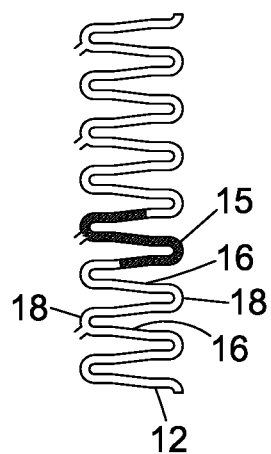

The stent 2 comprises a plurality of rings 12 joined by links 14. Each ring 12 comprises a repetition of S-shaped segments 15 of material, illustrated in FIG. 2C, defined by straight portions 16 extending between opposed bends 18, thereby defining a width for each ring. The repeated S-shaped segments may, for example, be joined along a centre line of each ring. The links 14 extend between facing bends 18 in adjacent rings 12, from every other facing bend 18 in one of the adjacent rings 12 to a corresponding every other facing bend 18 in the other one of the adjacent rings 12. As can be seen in the enlarged inserts in FIG. 2B, in some embodiments, the straight portions 16, while comparatively straight relative to the bends 18, are not strictly straight but rather have themselves three comparatively large radii of curvature between opposed bends 18, one adjacent each bend and one in between. It will, of course, be appreciated that in other embodiments the straight portions 16 may have other small deviations from a straight configuration or may be geometrically straight. More generally speaking, the bends 18 and straight portions 16 define a meander pattern for the stent material in the rings 12, which, in some embodiments may have varying inter-bend spacings resulting in a width that varies along a circumference of the ring. In such embodiments that use a repetition of S-shaped segments, the height of these segments may thus vary along the circumference.

The stent 2 comprises a first portion 20 and a second portion 22 extending from the first portion 20. The first portion 20 and second portion 22 are configured differently to facilitate the ability to longitudinally collapse the second portion 22 in a controlled manner by applying pressure to the malleable end 4 while retaining structural stability (as compared to conventional stents) of the first portion 20. These differences will now be described.

The links 14 in the first portion 20 are "V" shaped, that is they have two straight portions 24 joined by a bend 26. The links 14 in the second portion 22 are "Z" shaped, that is they have three straight portions 28 joined by bends 30. As a result, the links 14 in the second portion have a smaller lateral (circumferential) excursion of the bends 30 for a given longitudinal compression of the link 14 as compared to the excursion of bends 26 in the first portion 20. This facilitates controlled longitudinal collapse of the second portion with reduced risk of the bends 30 protruding too far into the vessel wall or lumen. Of course, it will be appreciated that other configurations with larger numbers of bends and straight portions can be employed in other embodiments, while achieving the same effect.

Further, the links 14 in the second portion 22 are thinner than the links 14 in the first portion, thus requiring less compression force to deform the links 14 in the second portion to facilitate longitudinal collapse without undue forces having to be applied by balloon inflation in the main lumen. In some embodiments, the width of the links in the second portion may be 60-80% of the width of the links in the first portion, for example 60, 70 or 80%. For example, some embodiments, the links in the first portion may have a width of 0.1 mm and the links in the second portion may have a width in the region of 60 to 80 μm, for example 60, 70 or 80 μm. In some embodiments, the width of the material in the rings 12 is the same in the first and second portions, for example 0.1 mm. In some embodiments, the overall length of the stent, end to end may be in the region of 10 to 20 mm, for example around 16 mm.

The rings 12 different in various aspects between the first and second portions, as well. Specifically, the relative orientation of adjacent rings may vary, as well as the overall length of the pattern defining the rings (or, correspondingly the widths of the rings 12, height of the S-shaped segments 15, or the length of the straight portions 16 in embodiments in which the straight portions 16/S-shaped segments 15 are of substantially constant length within each ring).

Regarding relative orientation, the bends 18 of the rings 12 in the first portion 20 are aligned such that bends 18 in adjacent rings facing each other across the gap between the rings 12 are aligned. In the second portion, the rings are aligned such that a given bend 18 in one ring is aligned with a bend 18 on the far side of an adjacent ring, that is with the given bend 18 being circumferentially between two bends 18 of the adjacent ring facing the given bend 18. It has been found that this arrangement of the relative orientation of adjacent rings in the second portion 22 (as compared to the first portion 20) imparts increased flexibility to the second portion 22, thus facilitating conforming (and maintaining conformity) of the second portion 22 with the lumen 6, in particular as the second portion 22 is longitudinally deformed to conform with the ostium as described above.

Regarding the length of the S-shaped segments in each ring 12, the total length of the meander (ring widths or links of straight portions—see above) is greater in the second portion 22 than in the first portion 20. Given the greater length as compared to the first portion 20, the second portion 22 is able to more readily expand radially than the first portion 20, facilitating the second portion 22 conforming to the shape of the lumen 6 in the region of the ostium and to cover a flared region of the ostium, as well as extending radially beyond the ostium into the lumen 8 when first placed. This provides a secure contact surface in the lumen 8 for a further stent that may be placed in the lumen 8. In embodiments where there are more than one ring 12 in the second portion 22, for example two rings as in the specific embodiment depicted in FIGS. 2 and 3, the length of the meander (or width of the ring/length of the straight portions) may be constant in the second portion 22 or may increase from one ring 12 to the next towards free end of the malleable end 4.

For example, in embodiments with two rings 12 in the second portion 22 along the lines depicted in FIG. 2A, the ring 12 adjacent the first portion 20 has straight portions 16 that are longer than those in the first portion 20. The ring 12 adjacent the free end has straight portions 16 longer than those of the other ring in the second portion 22. In a specific embodiment, the length of the straight portions 16 in the in the first portion 20, the ring 12 nearest to the first portion 20 in the second portion 22 and the ring 12 near the free end of the second portion 22 is 0.6, 0.8 and 1.0 mm, respectively, or more specifically in some embodiments 0.63, 0.80 and 1.00 mm. In other embodiments, along the lines depicted in FIG. 3, the rings 12 in the second portion 22 are all of substantially the same total length (longer than that in the first portion 20). For example, in some specific embodiments, the length of the straight portions 16 in the in the first portion 20, and in the second portion 22 is 0.6 and 0.8 mm, or more specifically in some embodiments 0.63 and 0.80 mm.

Figure 4A:
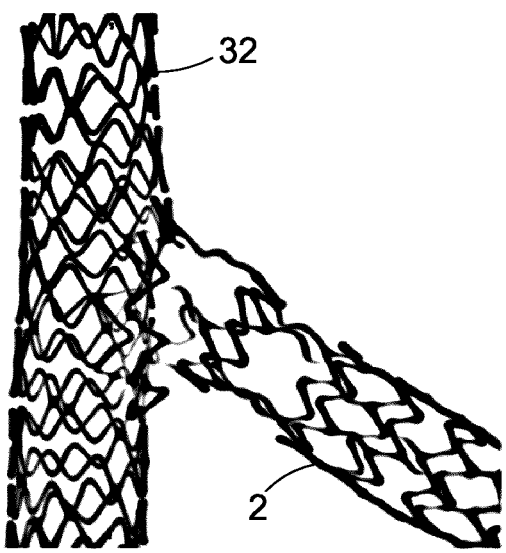
FIGS. 4A and 4B show micro computed tomography images of stents with a malleable end placed in a side branch.
Figure 4B:
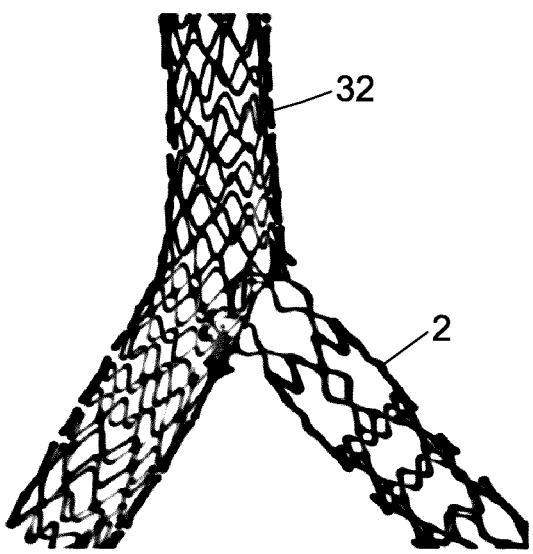

With reference to FIGS. 4A and 4B (each depicting a micro computer tomography image of placed and expanded stents), an actual stent deployment in a branched vessel structure in silicone bifurcation phantom model, with the stent placed in the side branch and a conventional stent 32 placed in the main branch, is illustrated. As described above with reference to FIGS. 1A, 1B and 1C, the stent 2 with malleable end 4 as described above is placed in and conformed to the side branch and ostium with two balloon inflations and the conventional stent 32 is then placed in the main branch to complete the deployment. A final-kissing inflation technique can be used to open the stent struts of the conventional stent crossing the ostium of the side branch at the end of the deployment procedure although this may not be necessary in some cases. This technique comprises inflating two balloons simultaneously, one in the main branch and one going across into the side branch through the struts of the conventional main branch stent and across the ostium of the side branch to open up the stent struts. As can be seen, the front end of the malleable end of the stent 2 conforms to both the main and site branch vessels to maintain an open lumen in the region of the ostium.

Having described specific embodiments above with reference to FIGS. 2A, 2B, 2C and 3, it will be apparent to the person skilled in the art of stent design that these specific embodiments have various differences between the first and second portions, which interact to provide a malleable end 4 that facilitates controlled longitudinal deformation for stent placement in a side branch, as described above. However, the skilled person will also appreciate that each of the differences described above makes a contribution to facilitating control of the longitudinal deformation. Controlled longitudinal deformation may thus be achieved with any combination of one or more of the differences between the first and second portions described above. Accordingly, the present disclosure encompasses all such embodiments, among which the skilled person will select in dependence upon the design goals and constraints.

Figure 5A:
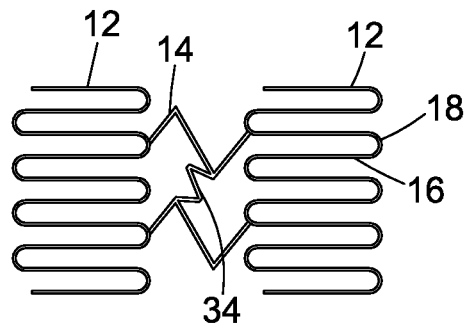
FIGS. 5A to 5F illustrate designs of a malleable end of a stent comprising cross links.
Figure 5B:
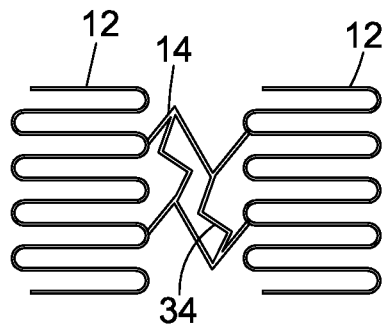
Figure 5C:
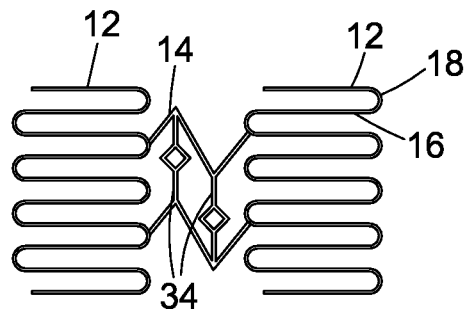
Figure 5D:
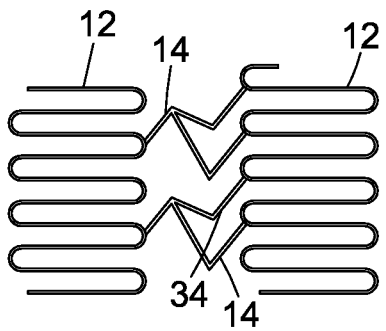
Figure 5E:
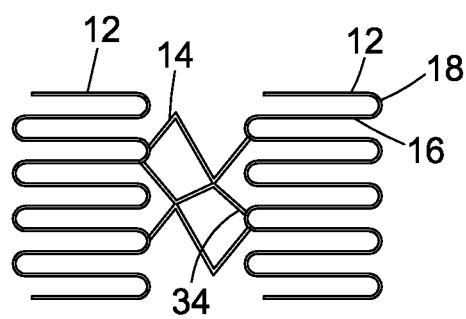
Figure 5F:
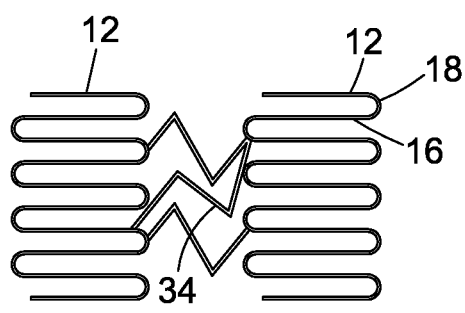

Additionally, in some applications, to maintain/improve radial strength in the malleable part of the stent, and in particular in the context of drug eluting stents for efficient drug delivery, it may be desirable to design stents with a smaller cell size compared to the designs discussed above while substantially maintaining in the malleability of the second portion. To this end, as now described with reference to FIGS. 5A to 5F, cell size may be reduced by introducing further links 34 between the links 14 in the second portion 22, or between the links 14 and straight portions 16 or bends 18 in an adjacent ring 12. For example, various embodiments are disclosed with the following arrangements:

- a "Z" shaped further link 34 between mutually closest bends of adjacent links 14 (FIG. 5A);
- "Z" shaped further links 34 between aligned bends of adjacent links 14 (FIG. 5B);
- further links 34 between aligned bends of adjacent links 14 comprising a quadrilateral arrangement of stent material portions (e.g. webs or struts—see FIG. 5C);
- further links 34 comprising such quadrilateral arrangements more generally;
- a further link 34 between a and of a link 14 and an adjacent bend 18 which is not connected to a link 14, for example the further link 34 being "V" shaped (FIG. 5D);
- a combination of further links 34 cross-linking between bends of adjacent links 14 and bends 18 of an adjacent ring (see FIG. 5E); and/or
- a further "Z" shaped link 34 linking a bend 18 on a given ring 12 linked by a given link 14 to a bend 18 on an adjacent ring 12 adjacent to be given ring 12, which bend 18 is linked by a link 14 adjacent the given link 14, or in other words adding a cross link 34 between bends 18 across a gap between rings, the bends 18 being spaced by an intervening unlinked bend 18 between the bends 18 linked by the further link 34 (see FIG. 5F).

Having read the above specific description of various embodiments, and will be apparent to the person skilled in the art that many modifications, alteration, reorganisations and juxtapositions of the features described above are possible without departing from the content of the present disclosure and which are within the scope of the invention defined in the claims that follow.

The invention claimed is:

1. A stent for use in vascular interventions, the stent comprising a first portion for placing in a first lumen and a second portion for placing in a region of a branch point at which the first lumen branches off a second lumen, the first portion comprising a plurality of rings linked together by first links, and the second portion having a free end and comprising two or more rings linked by second links to the first portion and together, each ring in the second portion being defined by a meander pattern extending between opposed bends spaced apart along the stent and each second link comprising three straight portions joined by a bend between each pair of straight portions, wherein respective ring widths in the second portion increase from one ring to the next towards the free end of the second portion, wherein the first links have a first width, the second links have a second width and the second width is less than the first width, and wherein bends on one side of each ring in the first portion are aligned with bends on an adjacent side of an adjacent ring in the first portion and bends on one side of each ring in the second portion are aligned with bends on a far side of an adjacent ring in the second portion.

2. A stent for use in vascular interventions, the stent comprising a first portion for placing in a first lumen and a second portion for placing in a region of a branch point at which the first lumen branches off a second lumen, the first portion comprising a plurality of rings linked together by first links, and the second portion having a free end and comprising two or more rings linked by second links to the first portion and together, each ring in the first portion being defined by a meander pattern extending between opposed bends spaced apart along the stent, each ring in the second portion being defined by a meander pattern extending between opposed bends spaced apart along the stent and each second link comprising three straight portions joined by a bend between each pair of straight portions, wherein respective meander lengths along the meander pattern of rings in the second portion are greater than respective meander lengths along the meander pattern of rings in the first portion and the meander lengths in the second portion increase from one ring to the next towards the free end of the second portion, wherein the first links have a first width, the second links have a second width and the second width is less than the first width, and wherein bends on one side of each ring in the first portion are aligned with bends on an adjacent side of an adjacent ring in the first portion and bends on one side of each ring in the second portion are aligned with bends on a far side of an adjacent ring in the second portion.

3. A stent according to claim 2, the two or more rings of the second portion comprising a first and a second ring, the first ring being joined to the first portion and to the second ring and the second ring defining the free end of the second portion.

4. A stent according to claim 2, wherein each meander pattern is defined by a repeating pattern of S-shaped segments.

5. A stent according to claim 4, wherein adjacent S-shaped segments are joined together along a center line of the respective ring.

6. A stent according to claim 4, wherein the S-shaped segments in the repeating pattern have the same size.

7. A stent according to claim 4, wherein the S-shaped segments in the repeating pattern have the same shape.

8. A stent according to claim 2, wherein the second portion is configured to deform longitudinally to conform with an ostium between the first lumen and the second lumen while remaining substantially conformal with the first lumen when the stent has been placed and expanded with the second portion in the region of the branch point and a balloon catheter is inflated in the second lumen to conform the second portion to the ostium.

9. A stent for use in vascular interventions, the stent comprising a first portion for placing in a first lumen and a second portion for placing in a region of a branch point at which the first lumen branches off a second lumen, the first portion comprising a plurality of rings linked together by first links, and the second portion comprising two or more rings linked by second links to the first portion and together, each ring in the first portion being defined by a meander pattern extending between opposed bends spaced apart along the stent, each ring in the second portion being defined by a meander pattern extending between opposed bends spaced apart along the stent and each second link comprising three straight portions joined by a bend between each pair of straight portions, wherein respective meander lengths along the meander pattern of rings in the second portion are greater than respective meander lengths along the meander pattern of rings in the first portion and the meander lengths in the second portion increase from one ring to the next towards a free end of the second portion;

wherein the first links have a first width, the second links have a second width and the second width is less than the first width;

wherein the two or more rings of the second portion comprise a first and a second ring, the first ring being joined to the first portion and to the second ring and the second ring defining the free end of the second portion;

wherein bends on one side of each ring in the first portion are aligned with bends on an adjacent side of an adjacent ring in the first portion and bends on one side of each ring in the second portion are aligned with bends on a far side of an adjacent ring in the second portion.

10. A stent according to claim 9, wherein respective ring widths in the second portion increase from one ring to the next towards the free end of the second portion.

11. A stent according to claim 9, wherein the meander pattern the of rings in the first portion is defined by a repeating pattern of S-shaped segments.

12. A stent according to claim 9, wherein the second portion is configured to deform longitudinally to conform with an ostium between the first lumen and the second lumen while remaining substantially conformal with the first lumen when the stent has been placed and expanded with the second portion in the region of the branch point and a balloon catheter is inflated in the second lumen to conform the second portion to the ostium.

13. A stent according to claim 12, wherein respective ring widths in the second portion increase from one ring to the next towards the free end of the second portion.

14. A stent for use in vascular interventions, the stent comprising a first portion for placing in a first lumen and a second portion for placing in a region of a branch point at which the first lumen branches off a second lumen, the first portion comprising a plurality of rings linked together by first links, and the second portion comprising two or more rings linked by second links to the first portion and together, each ring in the second portion being defined by a meander pattern extending between opposed bends spaced apart along the stent and each second link comprising three straight portions joined by a bend between each pair of straight portions, wherein respective meander lengths along the meander pattern of rings in the second portion are greater than respective meander lengths along a meander pattern of rings in the first portion and the meander lengths in the second portion increase from one ring to the next towards a free end of the second portion, wherein the first links have a first width, the second links have a second width and the second width is less than the first width, and wherein the second portion comprises third links, each third link linking a second link of the second links of the second portion with another second link of the second links of the second portion or with one of the rings in the first or second portion.

15. A stent according to claim 14, each third link linking two second links.

16. A stent according to claim 15, wherein each third link comprises three straight portions joined by a bend between each pair of straight portions.

17. A stent according claim 16, a first straight portion of the three straight portions of the third link being joined to a second link at one end and to a second straight portion of the three straight portions of the third link at the other end, and a third straight portion of the three straight portions of the third link being joined to a further second link at one end and to the second straight portion at the other end.

18. A stent according to claim 15, wherein each third link comprises four webs joined in a quadrilateral arrangement.

* * * * *